United States Patent

Bruna

Patent Number: 5,724,960
Date of Patent: Mar. 10, 1998

[54] INSERT DEFINING A MEASURING CHAMBER OF AN INHALER DEVICE

[75] Inventor: Pascal Bruna, Rouen, France

[73] Assignee: Valois S.A., Le Neubourg, France

[21] Appl. No.: 727,596

[22] PCT Filed: Apr. 12, 1995

[86] PCT No.: PCT/FR95/00474

§ 371 Date: Jan. 3, 1997

§ 102(e) Date: Jan. 3, 1997

[87] PCT Pub. No.: WO95/28980

PCT Pub. Date: Nov. 2, 1995

[30] Foreign Application Priority Data

Apr. 20, 1994 [FR] France ................... 94 04711

[51] Int. Cl.⁶ ........................................ A61M 15/00
[52] U.S. Cl. .................. 128/203.15; 128/203.12; 128/203.13; 128/203.21
[58] Field of Search ............... 128/203.15, 203.12, 128/203.13, 203.14, 203.18, 203.19, 203.21, 203.22, 203.23, 203.24, 200.24

[56] References Cited

U.S. PATENT DOCUMENTS

| 2,570,774 | 10/1951 | Dairs | 128/203.15 |
| 5,250,287 | 10/1993 | Cocozza | 128/203.21 |

FOREIGN PATENT DOCUMENTS

| 0488609 | 6/1992 | European Pat. Off. | 128/203.15 |
| 2 700 279 | 7/1994 | France | B05B 9/04 |
| 87 03 534 | 8/1987 | Germany | B05B 7/02 |
| WO 90/07351 | 7/1990 | WIPO | A61M 13/00 |
| WO 92/04068 | 3/1992 | WIPO | A61M 15/00 |
| WO 93/18812 | 9/1993 | WIPO | A61M 15/00 |

*Primary Examiner*—Vincent Millin
*Assistant Examiner*—V. Srivastava
*Attorney, Agent, or Firm*—Sughrue, Mion, Zinn, Macpeak & Seas, PLLC

[57] ABSTRACT

An inhaler device for inhaling substance in powder form, the device comprising a body (9), a compressed air pump (1) including a pump body (2) and a pump chamber (4), an expulsion duct (6) connected via a flap valve (5) to the pump chamber (4) and opening out into an outlet endpiece (7) through which the substance is dispensed, a substance reservoir (11) connected to said expulsion duct (6), and a substance measuring chamber (13) disposed fixedly in said expulsion duct (6), the device being characterized in that said measuring chamber (13) comprises an insert (14) having a top portion (16) projecting into said expulsion duct (6) in sealed manner through an opening provided for that purpose in said duct (6), said top portion (16) of said insert (14) being of a shape that is suitable for retaining a predetermined quantity of substance.

16 Claims, 2 Drawing Sheets

INSERT DEFINING A MEASURING CHAMBER OF AN INHALER DEVICE

BACKGROUND OF THE INVENTION

The present invention relates to an inhaler device for inhaling a substance in the form of a powder, and more particularly to an insert for accurately defining the measuring chamber of said inhaler device.

Powder inhalers are now very widespread, and one of their main applications lies in the field of pharmaceuticals, and in particular in the field of medication for treating asthma. One such inhaler is disclosed, in particular, in document EP-632 734.

Unfortunately, such medication is often very expensive and must be measured out accurately. In addition, dosage can vary between patients and also over a single course of treatment. It is therefore necessary to provide different inhaler devices depending on the quantity of substance that is to be dispensed.

To keep down the cost of manufacturing, and thus of selling, powder inhaler devices, it is consequently desirable during assembly to be able to vary in very simple manner the quantity of substance emitted on each occasion, i.e. to be able to vary the volume of the measuring chamber, with this being done by modifying as small a number of parts as possible.

DESCRIPTION OF THE RELATED ART

Documents WO-A-92/04068 and FR-2 700 279 disclose apparatuses each incorporating a measuring chamber that moves between a rest position where it is situated in the substance reservoir, and an actuation position where it is situated in the expulsion duct. The measuring chamber fills while in its rest position and is then displaced towards its actuation position by the user. That implementation suffers from several drawbacks: firstly it requires a complex mechanism for displacing the measuring chamber, thereby increasing the manufacturing cost of the apparatus; secondly since displacement of the measuring chamber needs to take place with relatively little lateral play, friction forces can arise that prevent the apparatus from operating properly; and further, during displacement of the measuring chamber, some of the substance can be lost, so dose reproducibility is not guaranteed.

SUMMARY OF THE INVENTION

An object of the invention is to provide means enabling the above-mentioned problem to be resolved while avoiding the above-mentioned drawbacks.

The present invention thus provides an inhaler device for inhaling substance in powder form, the device comprising a body, a compressed air pump including a pump body and a pump chamber, an expulsion duct connected via a flap valve to the pump chamber and opening out into an outlet endpiece through which the substance is dispensed, a substance reservoir connected to said expulsion duct, and a substance measuring chamber disposed fixedly in said expulsion duct, the device being characterized in that said measuring chamber comprises an insert having a top portion projecting into said expulsion duct in sealed manner through an opening provided for that purpose in said duct, said top portion of said insert being of a shape that is suitable for retaining a predetermined quantity of substance.

The term "fixedly disposed in said expulsion duct" means that the measuring chamber cannot be displaced out from the expulsion duct, but is on the contrary located at all times in said expulsion duct. Naturally, depending on its size, said measuring chamber may include end zones that extend beyond said expulsion duct, and it may also be deformable in configuration, while nevertheless permanently remaining disposed in the expulsion duct.

Preferably, while the substance is being expelled by the compressed air delivered by the pump to said expulsion duct, the measuring chamber is closed in sealed manner from the reservoir by means of a movable sealing device situated inside said reservoir.

Advantageously, said insert includes an undeformable bottom portion fixed to a support part, said support part being integral with the body of the device and having said expulsion duct passing therethrough, and a top portion extending said bottom portion and projecting into the expulsion duct in sealed manner, said top portion including a side wall that is approximately frustoconical in shape and that includes a recess in its central portion facing the reservoir to define the measuring chamber, the quantity of substance retained in said measuring chamber being expelled, on actuation of the device, along said expulsion duct towards said outlet endpiece by the compressed air delivered by the pump.

In a first embodiment of the invention, the entire insert is rigid and undeformable, its top portion projecting into the expulsion duct extending over a fraction of the height of said expulsion duct so as to keep a passage for compressed air along said expulsion duct.

Advantageously, said insert includes a stud beneath said recess defining the measuring chamber, the stud extending to a fixed element of the device and bearing thereagainst to reinforce the rigidity of said insert. By way of example, this fixed element may be the pump body.

Another object of the invention is to guarantee complete sealing of the dose of substance to be dispensed until the moment it is expelled from the inhaler. A major drawback of certain inhalers is that between the moment when the measuring chamber is filled with the dose of substance to be ejected, and the moment when the device is indeed actuated, said dose of substance is situated in the expulsion duct in contact with the air. If the device is not actuated immediately after the measuring chamber has been loaded, the substance can therefore become contaminated, and if the device is used in humid conditions, the powder can clump together under the effect of moisture. The substance will then be dispensed in compact form, thus losing a major portion of its effectiveness. The present invention therefore also has the object of providing an inhaler device which includes a measuring chamber that is completely sealed until the device is actuated, thereby avoiding the above-specified drawbacks.

In a second embodiment, the present invention thus also provides an inhaler device including an insert in which said top portion of said insert is deformable under the effect of the pressure of the compressed air, said top portion of the insert extending over the entire height of the expulsion duct to press against the top wall thereof and thus close the duct when the device is not actuated, said measuring chamber consequently being isolated in completely sealed manner from the reservoir by a movable sealing device situated inside the reservoir, and from the expulsion duct by the top portion of the insert.

Preferably, said top proton of said insert includes a thin zone in its side wall where the top portion of the insert joins the bottom portion of the insert, the thin zone forming a flexible hinge where said top portion of said insert deforms under the action of the force exerted by the compressed air during actuation of the device to release a passage for the compressed air, and returns to its initial shape when the device is at rest.

Advantageously, said recess defining the measuring chamber is undeformable and moves downwards in translation away from the top wall of the expulsion duct when said thin zone deforms during actuation of the device, thereby releasing said passage for the compressed air along said expulsion duct, enabling all of the substance situated inside said measuring chamber to be expelled. This implementation of the invention makes it possible to ensure that the insert returns to its initial shape after each use, and that the measuring chamber always retains the same volume and therefore always dispenses the same quantity of substance.

To avoid possible deformation of said recess while the insert is deforming, said top portion of the insert includes a stud beneath said recess and extending at rest to a point that is situated at a distance from a fixed element of the device, and coming into abutment thereagainst during actuation of the device, thereby limiting deformation of said insert and limiting translation of said recess, thus defining a calibrated passage for the compressed air.

Advantageously, said top portion of the insert includes one or more ribs or grooves in its side wall, thereby accurately defining the location where the thin zone is to deform during actuation of the device.

According to the invention, the shape of said insert in horizontal section may be circular, oblong, or rectangular.

Advantageously, said insert is made as a single piece and it can be fixed to said support part by mutual engagement or by snap-fastening.

To guarantee good sealing between the insert and the expulsion duct, it is advantageous to make said insert out of a material that is sufficiently flexible, e.g. such as an elastomer.

Other characteristics and advantages of the present invention appear from the following description of two embodiments of the invention given as non-limiting examples and with reference to the accompanying drawings.

DESCRIPTION OF THE PREFERRED EMBODIMENTS

Figure 1:
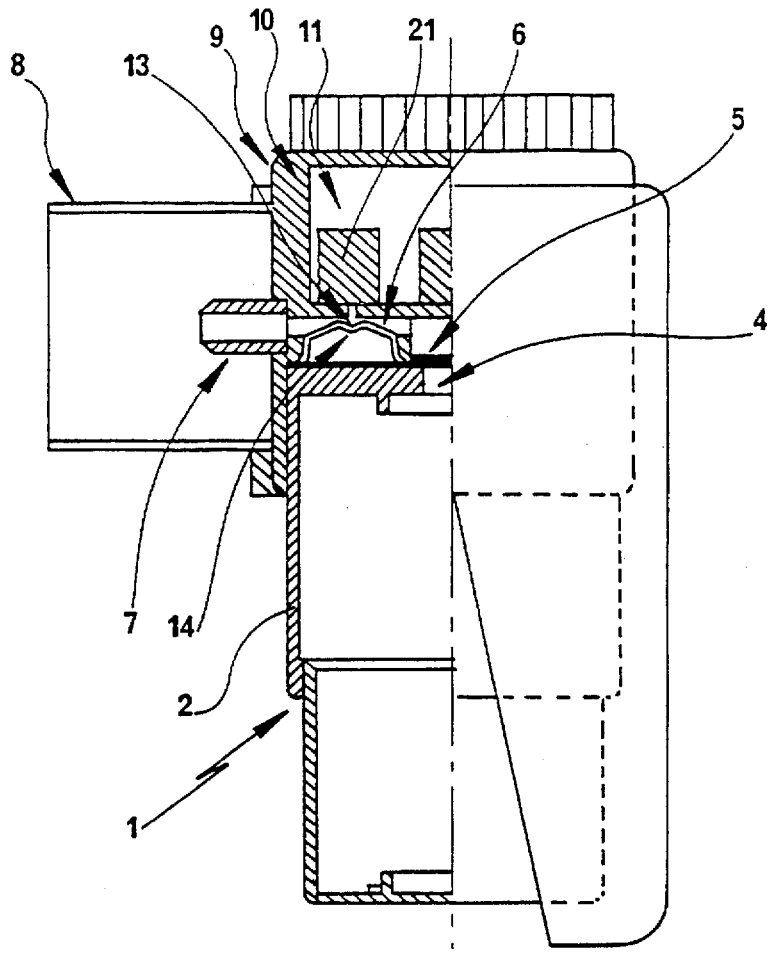
FIG. 1 is a diagrammatic general view of the inhaler device of the invention.

With reference to FIG. 1, the inhaler device includes a compressed air pump 1 comprising a pump body 2 and a pump chamber 4, said pump 1 being designed to expel compressed air when the device is actuated. Said pump chamber 4 is connected via a flap valve 5 to an expulsion duct 6 which is itself connected to an outlet endpiece 7 opening out into an inhaler member 8 suitable for facilitating inhalation by the patient. By way of example, the endpiece 8 may be a mouthpiece if the substance is administered by mouth. The device also includes a body 9 comprising a support part 10 which supports the outlet endpiece 7 and said inhaler member 8, and said expulsion duct 6 passes therethrough. Advantageously, the pump 1 can be separated from the remainder of the device and said pump body 2 can be snap-fastened to said body 9 of the device during assembly. Nevertheless, the pump body 2 and the body 9 of the device may equally well be integral with each other. The device also includes a substance reservoir 11 connected to said expulsion duct 6 via a small hole 12. The reservoir is preferably situated above the expulsion duct 6, as shown in the figures. Said small hole 12 forms a portion of the measuring chamber 13 which opens out into the expulsion duct 6 and which comprises an insert 14 having a top portion 16 projecting into said expulsion duct 6. The insert 14 has a bottom portion 15 which may advantageously be cylindrical, but which could equally well be oblong or rectangular in shape in horizontal section. This bottom portion 15 of the insert 14 is fixed on said support part 10 of the body 9 of the device, advantageously by mutual engagement or by snap-fastening by means of tabs 17. The bottom portion 15 of the insert 14 is extended by a top portion 16 that projects into the expulsion duct 6 via an opening provided for this purpose in said duct. For proper operation of the device, the insert 14 must be inserted into the expulsion duct in sealed manner. It is essential for the bottom portion 15 of the insert, situated outside the expulsion duct, to be undeformable and to remain fixedly in sealing contact with the support part 10 throughout operation of the device in order to avoid any leakage. Advantageously, the insert 14 is made of relatively flexible material making it possible to provide said sealing at the opening into the duct through which the insert penetrates into the duct.

The measuring chamber 13 is therefore disposed at all times in and immediately around the expulsion duct 6 and there is no need to provide a complex mechanism for displacing said measuring chamber out from said duct. It can therefore be said that the measuring chamber 13 is fixedly disposed in said expulsion duct 6.

Also, in order to provide sealing relative to the reservoir 11 while the device is in operation, the small hole 12 of the measuring chamber 13 is closed in sealed manner by a movable sealing device 21 situated inside said reservoir 11. The sealing device 21 is removed from the hole 12 to allow substance to be loaded into the measuring chamber 13, and then it is put into place in order to enable the device to be actuated.

The top portion 16 of the insert 14 projecting into the expulsion duct 6 is approximately frustoconical in shape, having a side wall 14 that extends from said bottom portion 15, and in its central portion facing the hole 12 it has a recess 19 adapted to retain a measured dose of substance and defining the measuring chamber 13.

Figure 2:
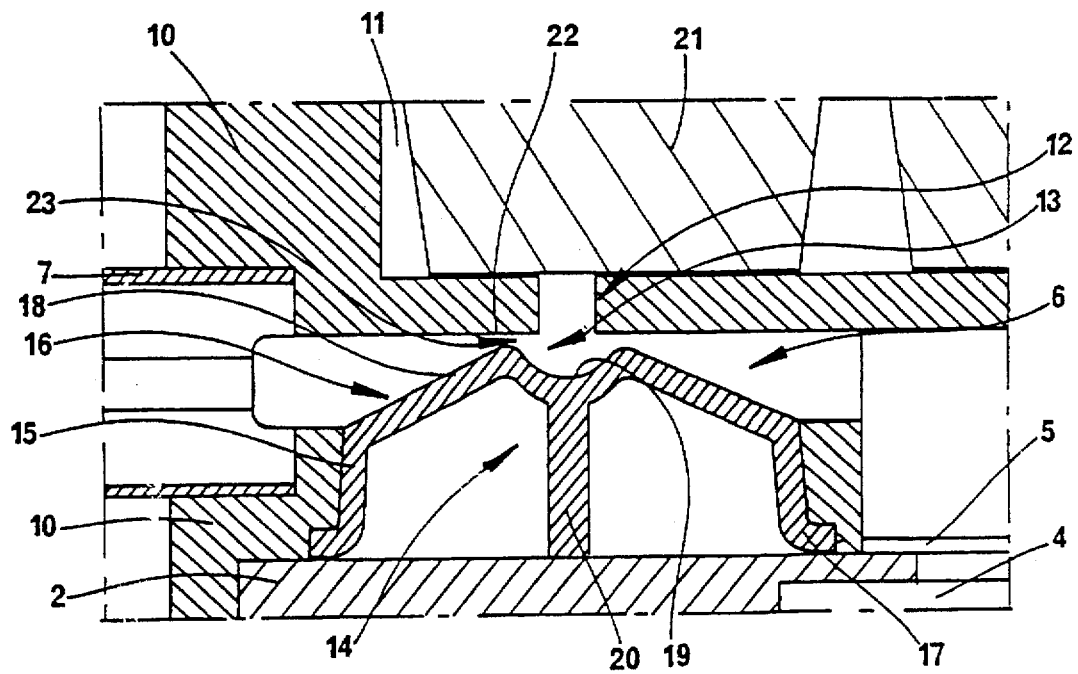
FIG. 2 is a view on a larger scale of the portion of the inhaler device that includes the measuring chamber, in a first embodiment of the invention.
Figure 3A:
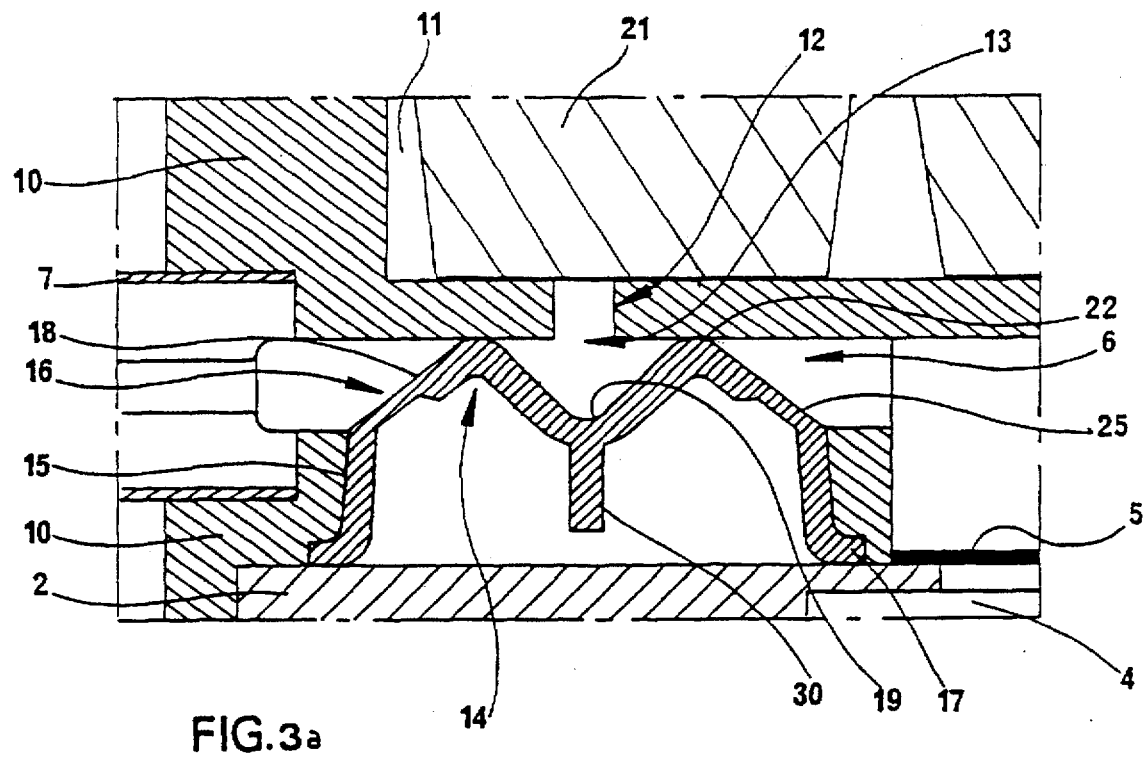
FIG. 3a is a view similar to that of FIG. 2, but relates to a second embodiment of the invention while at rest.
Figure 3B:
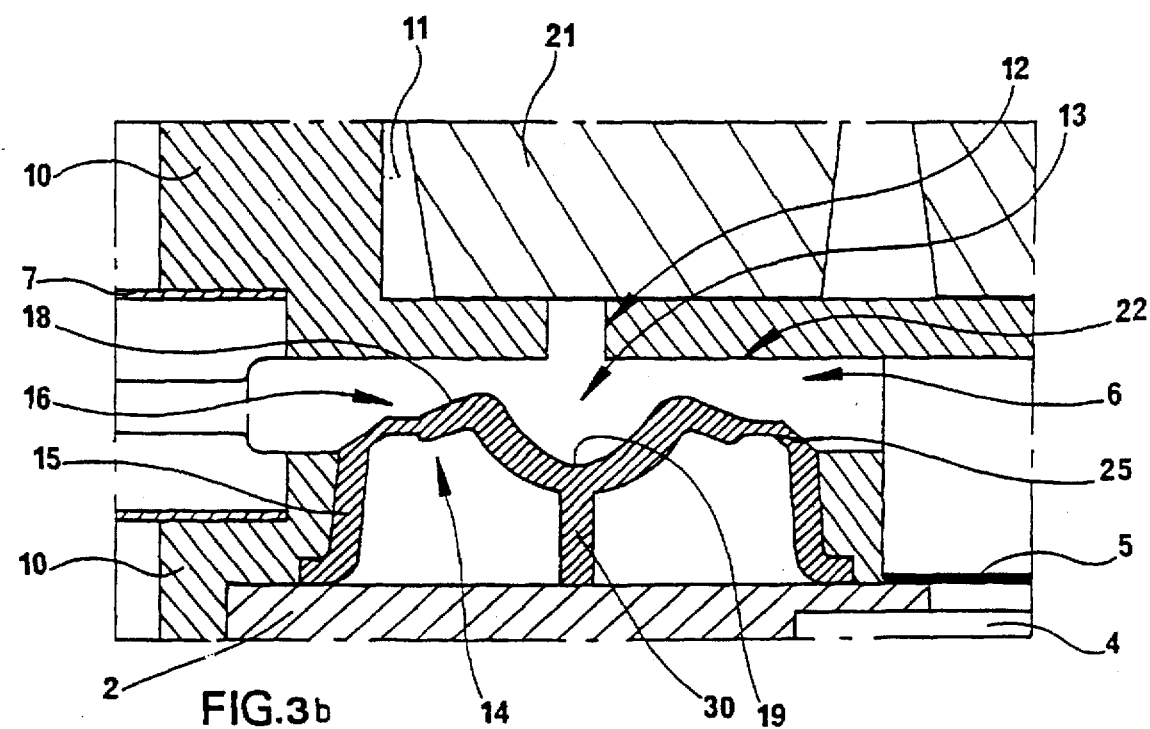
FIG. 3b is the same view as FIG. 3a but while the device is in operation.

A first embodiment of the invention is shown in FIG. 2. In this embodiment, the entire insert 14 is rigid and undeformable. The side wall 18 of its top portion 14 therefore extends solely over a fraction of the height of the expulsion duct and it does not press against the top wall 22 of said duct so as to ensure that a passage 22 is guaranteed through which compressed air can pass along said duct 6 when the device is actuated. Thus, a cycle for expelling a dose of substance comprises the following steps:

The sealing device 21 situated inside the reservoir 11 is removed from the hole 12, i.e. from the measuring chamber 13, and the chamber is filled with substance. The substance thus falls through the hole 12 under gravity or with assistance from external means into the recess 19 of the insert 14.

When the measuring chamber 13 (recess 19 plus hole 12) is full, the sealing device 21 of the reservoir recloses said hole 12 in sealed manner. The device is then actuated and compressed air from the pump 1 passes from the pump chamber 4 into the expulsion duct 6 via the duct 5 and subsequently completely empties the measuring chamber 13 of the substance it contains by flowing via the passage 23. Said dose of substance is thus dispensed in powder form via the outlet endpiece 7 into the inhalation member 8 and thus into the patient.

Advantageously, since the pressure of the compressed air can be high, the insert 14 is stiffened by providing a stud 20 disposed beneath said recess 19 of the insert 14 and extending from said recess 19 to a fixed element of the device, e.g. the pump body 2 as shown in the figures, against which element it presses. The stud 20 may be integral with the insert 14.

A second embodiment of the invention is shown in FIGS. *3a* and *3b*. In this embodiment, the top portion 16 of the insert 14 is deformable under the effect of the pressure of the compressed air, and the side wall 18 extends over the full height of the expulsion duct 6 so as to press against the top wall 22 thereof. At rest, the expulsion duct 6 is thus closed by the insert 14 and the measuring chamber 13 is consequently completely sealed when the device is not actuated. In the reservoir 11, sealing is provided by the above-mentioned movable sealing device 21 located inside the reservoir 11, and inside the expulsion duct 6 sealing is provided by the insert 14. This absolute sealing prevents substance being contaminated between the moment when the measuring chamber 16 is filled and the moment when it is emptied by actuating the device. Thus, should a certain amount of time elapse between said filling and said emptying, the substance is preserved from possible external humidity which might otherwise reduce the effectiveness of the ejected dose, e.g. by causing the powder to clump. Consequently, this embodiment of the invention is advantageous.

As mentioned above, the top portion 16 of the insert 14 is thus deformable under the effect of the pressure of the compressed air. Thus, when the device is actuated, the compressed air delivered into the expulsion duct 6 from the pump 1 via the pump chamber 4 and the valve 5 comes into abutment against the side wall 18 of the insert and causes the insert to become deformed, thereby releasing a passage for the compressed air within the expulsion duct. The compressed air can thus completely empty the measuring chamber 13, with the substance being conveyed to the outlet endpiece 7 and then dispensed to the patient via the inhaler member 8. It should be observed that even if a portion of the measuring chamber 13 is deformable, said portion remains permanently in the expulsion duct 6.

Advantageously, the top portion 16 of the insert 14 includes a thin zone 25 in its side wall 18 where the top portion 16 of the insert 14 meets the bottom portion 25 thereof. This thin zone 25 serves to form a kind of flexible and resilient hinge which folds under the effect of the pressure of the compressed air so as to release said passage for the compressed air, and it returns to its initial shape as soon as there is no longer any compressed air in the expulsion duct 6. During deformation of the insert 14, the recess 19 defining the measuring chamber 13 preferably does not itself deform, merely moving in translation away from the top wall 22 of the expulsion duct 6. This preferred implementation of the invention ensures that the volume of substance contained in the measuring chamber 13 does not vary even after the device has been actuated several times, i.e. after the insert 14 has been deformed several times. To prevent deformation of the insert 14 being excessive, which would give rise to deformation of the recess 19, it is advantageous to provide a stud 30 beneath the recess 19. As shown in the figures, this stud is generally integral with the insert 14, and at rest, it extends to a point that is situated at a distance from a fixed element of the device, e.g. the pump body 2, and it comes into abutment thereagainst when the device is actuated, thus limiting deformation of the insert 14 and translation of the recess 19, said stud 30 also defining a calibrated passage for the compressed air, thus ensuring that dispensing is performed identically for each dose of substance.

To determine accurately the location where the thin zone 25 of the insert 14 is to deform when the device is actuated, one or more ribs or grooves (not shown) may be provided on the side wall 18 of the insert.

Advantageously, the insert 14 of the invention is made as a single piece and may be made out of elastomer or any other material that is sufficiently flexible, deformation of said insert being due either to the material from which it is made or to the shape of said insert, as described above.

I claim:

1. An inhaler device for inhaling substance in powder form, the device comprising a body (9), a compressed air pump (1) including a pump body (2) and a pump chamber (4), an expulsion duct (6) connected via a flap valve (5) to the pump chamber (4) and opening out into an outlet endpiece (7) through which the substance is dispensed, a substance reservoir (11) connected to said expulsion duct (6), and a substance measuring chamber (13) disposed fixedly in said expulsion duct (6), the device being characterized in that said measuring chamber (13) comprises an insert (14) having a top portion (16) projecting into said expulsion duct (6) in sealed manner through an opening provided for that purpose in said duct (6), said top portion (16) of said insert (14) being of a shape that is suitable for retaining a predetermined quantity of substance.

2. An inhaler device according to claim 1, in which, while the substance is being expelled by the compressed air delivered by the pump (1) to said expulsion duct (6), the measuring chamber (13) is closed in sealed manner from the reservoir (11) by means of a movable sealing device (21) situated inside said reservoir (11).

3. An inhaler device according to claim 1, in which said insert (14) includes an undeformable bottom portion (15) fixed to a support part (10), said support part being integral with the body (9) of the device and having said expulsion duct (6) passing therethrough, and a top portion (16) extending said bottom portion (15) and projecting into the expulsion duct (6) in sealed manner, said top portion (16) including a side wall (18) that is approximately frustoconical in shape and that includes a recess (19) in its central portion facing the reservoir (11) to define the measuring chamber (13), the quantity of substance retained in said measuring chamber (13) being expelled, on actuation of the device, along said expulsion duct (6) towards said outlet endpiece (7) by the compressed air delivered by the pump (1).

4. An inhaler device according to claim 1, in which the entire insert (14) is rigid and undeformable, its top portion (16) projecting into the expulsion duct (6) extending over a fraction of the height of said expulsion duct (6) so as to keep a passage (23) for compressed air along said expulsion duct (6).

5. An inhaler device according to claim 3, in which said insert (14) includes a stud (20) beneath said recess (19) defining the measuring chamber (13), the stud (20) extending to a fixed element of the device and bearing thereagainst to reinforce the rigidity of said insert (14).

6. An inhaler device according to claim 5, in which said fixed element of the device is the pump body (2).

7. An inhaler device according to claim 1, in which said top portion (16) of said insert (14) is deformable under the effect of the pressure of the compressed air, said top portion (16) of the insert (14) extending over the entire height of the expulsion duct (6) to press against the top wall (22) thereof and thus close the duct when the device is not actuated, said measuring chamber (13) consequently being isolated in completely sealed manner from the reservoir (11) by a movable sealing device (21) situated inside the reservoir (10), and from the expulsion duct (6) by the top portion (16) of the insert (14).

8. An inhaler device according to claim 7, in which said top proton (16) of said insert (14) includes a thin zone (25) in its side wall (18) where the top portion (16) of the insert (14) joins the bottom portion (15) of the insert (14), the thin zone (25) forming a flexible hinge where said top portion (16) of said insert (14) deforms under the action of the force exerted by the compressed air during actuation of the device to release a passage for the compressed air, and returns to its initial shape when the device is at rest.

9. An inhaler device according to claim 8, in which said recess (19) defining the measuring chamber (13) is undeformable and moves downwards in translation away from the top wall (22) of the expulsion duct (6) when said thin zone (25) deforms during actuation of the device, thereby releasing said passage for the compressed air along said expulsion duct (6), enabling all of the substance situated inside said measuring chamber (13) to be expelled.

10. An inhaler device according to claim 9, in which said top portion (16) of the insert (14) includes a stud (30) beneath said recess (19) and extending at rest to a point that is situated at a distance from a fixed element of the device, and coming into abutment thereagainst during actuation of the device, thereby limiting deformation of said insert (14) and limiting translation of said recess (19), thus defining a calibrated passage for the compressed air.

11. An inhaler device according to claim 10, in which said fixed element of the device is the pump body (2).

12. An inhaler device according to claim 8, in which said top portion (16) of the insert (14) includes one or more ribs or grooves in its side wall (18), thereby accurately defining the location where the thin zone is to deform during actuation of the device.

13. An inhaler device according to claim 1 in which said insert (14) is made as a single piece.

14. An inhaler device according to claim 1 in which said insert (14) is fixed to said support part (10) by mutual engagement or by snap-fastening.

15. An inhaler device according to claim 1 in which said insert (14) is made of flexible material.

16. An inhaler device according to any preceding claim, in which said insert (14) is oblong in shape in horizontal section.

* * * * *